(12) United States Patent
Bhat et al.

(10) Patent No.: US 10,052,326 B1
(45) Date of Patent: Aug. 21, 2018

(54) ANTIHEPATOTOXIC AGENTS

(71) Applicant: KING SAUD UNIVERSITY, Riyadh (SA)

(72) Inventors: Mashooq Ahmad Bhat, Riyadh (SA); Mohamed Abdulrahman Al-Omar, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/782,462

(22) Filed: Oct. 12, 2017

(51) Int. Cl.
| | |
|---|---|
| *C07D 405/08* | (2006.01) |
| *A61K 31/357* | (2006.01) |
| *A61K 31/513* | (2006.01) |
| *A61K 31/12* | (2006.01) |
| *C07D 409/08* | (2006.01) |
| *A61K 31/506* | (2006.01) |
| *A61K 31/385* | (2006.01) |

(52) U.S. Cl.
CPC ............ *A61K 31/513* (2013.01); *A61K 31/12* (2013.01); *A61K 31/357* (2013.01); *A61K 31/385* (2013.01); *A61K 31/506* (2013.01); *C07D 405/08* (2013.01); *C07D 409/08* (2013.01)

(58) Field of Classification Search
CPC .. C07D 405/08; C07D 409/08; A61K 31/357; A61K 31/385; A61K 31/506
See application file for complete search history.

(56) References Cited

U.S. PATENT DOCUMENTS

| | | | |
|---|---|---|---|
| 6,130,243 A | 10/2000 | Takahashi et al. | |
| 6,313,160 B1 | 11/2001 | Guillaumet et al. | |
| 6,376,535 B2 | 4/2002 | Ohshima et al. | |
| 6,632,955 B1 | 10/2003 | Shibasaki et al. | |
| 7,332,484 B2 | 2/2008 | Singh et al. | |
| 9,119,856 B1 | 9/2015 | Al-Dhfyan et al. | |
| 2008/0145453 A1 | 6/2008 | Lopez et al. | |
| 2011/0092585 A1 | 4/2011 | Khanuja et al. | |

OTHER PUBLICATIONS

Jaeschke et al., Mechanisms of Hepatotoxicity, Toxicological Sciences, 65, pp. 166-176 (2002).*
Mehta et al., Drug-induced Hepatotoxicity, Medscape Article 169814, pp. 1-25 (2016).*
Singh et al., Drug-induced Liver Toxicity and Prevention by Herbal Antioxidants: An Overview, Frontiers in Physiology, vol. 6, Article 363, pp. 1-18 (2016).*
Khan et al., CCl4-induced hepatotoxicity: protective effect of rutin on p53, CYP2E1 and the antioxidative status in rat, BMC Complementary and Alternative Medicine, 12:178, pp. 1-6 (2012).*

* cited by examiner

*Primary Examiner* — Deepak R Rao
(74) *Attorney, Agent, or Firm* — Richard C Litman

(57) ABSTRACT

Antihepatotoxic agents include dihydropyrimidinone derivatives with 1,4-benzodioxane. The antihepatotoxic agents are compounds having the structural formula represented by Formula 1:

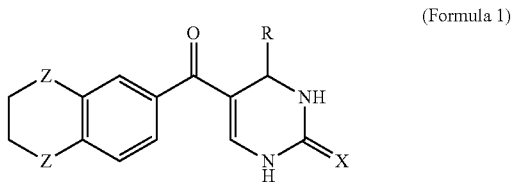

(Formula 1)

wherein each Z independently represents O, N or S; X represents O or S; R represents aryl, substituted aryl, heteroaryl, or substituted heteroaryl; and pharmaceutically acceptable salts of these compounds.

19 Claims, 6 Drawing Sheets

Effect of DHPB-2 on Serum Marker Enzymes of Control and Experimental Animals

| Treatments (n=6) | Dose (mg/kg) | AST (U/L) Mean ± SE | % Change | ALT (U/L) Mean ± SE | % Change |
|---|---|---|---|---|---|
| Normal | | 111.76±3.72 | | 28.78±1.69 | |
| $CCl_4$ | 1.5 mL | 386.83±9.95***[a] ↑ | 62.77 | 335.16±6.04***[a] ↑ | 69.53 |
| Silymarin +$CCl_4$ | 10 | 144.00±7.44***[b] ↓ | | 102.10±6.71***[b] ↓ | 12.28 |
| DHPB-2+ $CCl_4$ | 10 | 383.33±6.05 [b] | 46.53 | 294.00±10.76**[b] ↓ | 57.03 |
| DHPB-2+ $CCl_4$ | 20 | 206.83±7.34***[b] ↓ | | 144.00±3.86***[b] ↓ | |

All values represent mean ± SEM. $p<0.01$, *$p<0.001$; ANOVA, followed by Dunnett's multiple comparison test.

[a] As compared with Normal group.
[b] As compared with $CCl_4$ group.

FIG. 2A

| ALP (U/L) | | GGT (U/L) | | Bilirubin (mg/dL) | |
|---|---|---|---|---|---|
| Mean ± SE | % Change | Mean ± SE | % Change | Mean ± SE | % Change |
| 385.16±14.19 | | 4.68±0.23 | | 0.60±0.01 | |
| 601.83±7.98***[a] ↑ | 26.53 | 17.00±0.67***[a] ↑ | 60.58 | 3.01±0.10***[a] ↑ | 65.75 |
| 442.16±13.51***[b] ↓ | | 6.70±0.24***[b] ↓ | 20.28 | 1.03±0.05***[b] ↓ | |
| 576.16±15.74[b] | 4.26↓ | 13.50±0.59**[b] ↓ | | 2.83±0.06[b] | 6.02↓ |
| 452.16±13.79***[b] ↓ | 24.86 | 7.81±0.31***[b] ↓ | 54.01 | 1.49±0.07***[b] ↓ | 50.49 |

FIG. 2B

Effect of DHPB-2 on Metabolism and Serum Lipoproteins of Control and Experimental Animals

| Treatments (n=6) | Dose (mg/kg) | Cholesterol (mg/dL) Mean ± SE | % Change | Triglycerides (mg/dL) Mean ± SE | % Change |
|---|---|---|---|---|---|
| Normal | | 89.66±1.68 | | 71.63±1.83 | |
| $CCl_4$ | 1.5 mL | 189.66±3.95***[a] | ↑ | 183.50±4.63***[a] | ↑ |
| Silymarin+ $CCl_4$ | 10 | 130.00±3.72***[b] | 31.45 ↓ | 116.76±7.39***[b] | 36.36 ↓ |
| DHPB-2+ $CCl_4$ | 10 | 175.33±4.91*[b] | 7.55 ↓ | 172.33±2.92 [b] | 6.08 ↓ |
| DHPB-2+ $CCl_4$ | 20 | 141.66±2.36***[b] | 24.25 ↓ | 136.83±3.80***[b] | 25.97 ↓ |

All values represent mean ± SEM. $*p<0.05$; $***p<0.001$; ANOVA, followed by Dunnett's multiple comparison test.

[a] As compared with Normal group.

[b] As compared with $CCl_4$ group.

FIG. 3A

| HDL (mg/dL) | | LDL (mg/dL) | | VLDL (mg/dL) | |
|---|---|---|---|---|---|
| Mean ± SE | % Change | Mean ± SE | % Change | Mean ± SE | % Change |
| 57.58±2.28 | | 17.75±1.13 | | 14.32±0.36 | |
| 23.61±0.93***[a] | ↓ | 129.35±4.74***[a] | | 36.70±0.92***[a] | |
| 51.06±2.75***[b] | 116.23 ↑ | 55.58±2.07***[b] | 57.03 ↓ | 23.35±1.47***[b] | 36.36 ↓ |
| 26.11±0.62*[b] | 10.58 ↑ | 114.75±4.86 [b] | 11.28 ↓ | 34.46±0.58 b | 6.08 ↓ |
| 48.26±2.27***[b] | 104.37 ↑ | 68.23±1.52***[b] | 47.24 ↓ | 27.16±0.76***[b] | 25.97 ↓ |

FIG. 3B

ANTIHEPATOTOXIC AGENTS

BACKGROUND

1. Field

The present subject matter relates to antihepatotoxic compounds, compositions containing these compounds, and the preparation and use of these compounds and compositions.

2. Description of the Related Art

Liver disease is a leading cause of death in many countries. Liver disease can be caused by malnutrition, alcohol consumption, continuous exposure to environmental pollutants, and a wide variety of drugs, chemicals, toxins, bacteria, viruses and parasites. The liver is continuously exposed to a variety of xenobiotics, therapeutic agents and environmental pollutants, leading to various liver disorders such as acute viral hepatitis, chronic viral hepatitis, liver cirrhosis and drug induced liver damage. So far, no effective measures are available for the treatment of liver diseases except some naturally occurring medicinal plants. Silymarin isolated from the seeds of *Silybum marianum*, commonly known as Milk thistle, has been used as a potent antihepatotoxic agent against a variety of toxicants. The isolated silymarin is a mixture of three isomers, namely, silybin, silydianin and silychristin. Silybin is the most active component, containing 1,4-benzodioxane ring system, whereas the other two isomers do not include 1,4-benzodioxane moieties, and thus do not exhibit significant antihepatotoxic activity.

Pyrimidines have played an important role in medicinal chemistry. Pyrimidines are important scaffolds in the field of medicinal chemistry because of their biological activities, such as anti-tumor, anti-virus and anti-bacterial activity. Some pyrimidines have been used as potential anti-hypertensive agents. For example, 4-Aryl-1,4-dihydropyridines, such as Nifedipine, were first introduced as antihypertensive drugs in 1975. Dihydropyridines are the most potent calcium channel modulators available for the treatment of various cardiovascular diseases. Dihydropyrimidines, popularly known as Biginelli's compounds, are associated with a broad spectrum of biological activities.

SUMMARY OF THE SUBJECT MATTER

The present subject matter relates to antihepatotoxic agents. The antihepatotoxic agents include dihydropyrimidinone derivatives with 1,4-benzodioxane. These compounds exhibit antihepatotoxic activity in patients. The compounds are simple, low molecular weight compounds demonstrating favorable activity compared to other agents commonly used for treating or preventing liver disease such as silybin, the major active constituent of silymarin.

The antihepatotoxic agents include 5-(2,3-dihydro-1,4-benzodioxine-6-carbonyl)-4-(substituted phenyl-3,4-dihydropyrimidin-2(1H)-one derivatives having the structure represented by Formula 1:

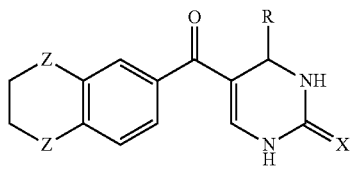

(Formula 1)

wherein
each Z independently represents O, N, or S;
X represents O or S; and R represents aryl, substituted aryl, heteroaryl, or substituted heteroaryl;
or a pharmaceutically acceptable salt thereof.

wherein each Z independently represents O, N or S; X represents O or S; R represents aryl, substituted aryl, heteroaryl, or substituted heteroaryl. The present subject matter also includes a pharmaceutically acceptable salt of any of these compounds, and associated pharmaceutical compositions incorporating the compounds, as well as use of these compounds and compositions for treating or preventing acute or chronic viral hepatitis, liver cirrhosis, or drug-induced liver damage.

One embodiment relates to compounds having the structure of Formula 1:

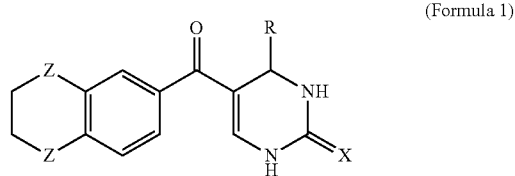

(Formula 1)

wherein
each Z independently represents O, N, or S;
X represents O or S; and R represents aryl, substituted aryl, heteroaryl, or substituted heteroaryl;
or a pharmaceutically acceptable salt thereof.

In an embodiment of the compound of Formula 1, R is: 2-nitro phenyl; 3-nitro phenyl; 4-nitro phenyl; 4-chloro phenyl; 3,4-dimethoxy phenyl; 2-methoxy phenyl; 3-methoxy phenyl; 4-methoxy phenyl; or 4-ethoxy phenyl.

In an embodiment of the compound of Formula 1, R is substituted heteroaryl, e.g., heteroaryl substituted with halogen, alyl, haloalyl, alkoxy, haloalkoxy, alkylthio, alkylamino, heteroaryl, aryloxy, haloaryloxy, arylthio, or arylamino.

A further embodiment relates to methods of treating or preventing hepatotoxicity in a patient, using one or more of the compounds of Formula 1.

Another embodiment relates to methods of preparing a compound of Formula 1, including the steps of: refluxing 1-(2,3-dihydro-1,4-benzodioxin-6-yl)ethan-1-one (0.01 mol) with dimethylformamide dimethylacetal (DMF-DMA) (0.013 mol) to obtain an enaminone; preparing or obtaining a solution including the enaminone, substituted benzaldehyde, urea; and Glacial acetic acid, refluxing the solution to yield the compound of Formula 1.

Other embodiments relate to preparation of pharmaceutical compositions including at least one compound of Formula 1 for treating or preventing hepatotoxicity in a patient.

Yet another embodiment relates to the preparation or use of one or more of the compounds identified below as DHPB 1-10 for treating or preventing hepatotoxicity in a patient.

These and other features of the present subject matter will become readily apparent upon further review of the following specification and drawings.

BRIEF DESCRIPTION OF THE DRAWINGS

FIGS. 2A-2B together show a single table showing the effects of DHPB-2 on serum marker enzymes, in a multiple comparison test including a control.

FIGS. 3A-3B together show a single table showing the effects of DHPB-2 on metabolism and serum lipoproteins, in a multiple comparison test including a control.

DETAILED DESCRIPTION

Figure 1:
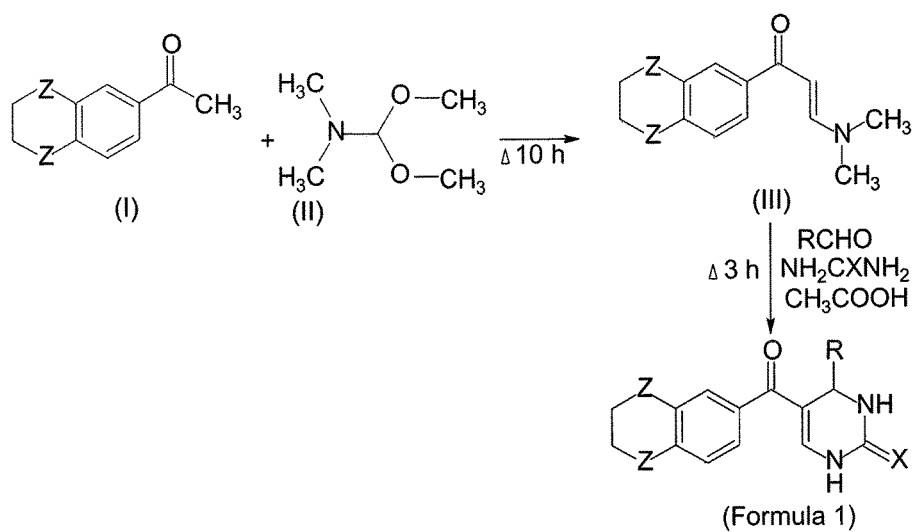
FIG. 1 shows a reaction scheme for synthesizing the compounds of Formula 1.
Figure 4A:
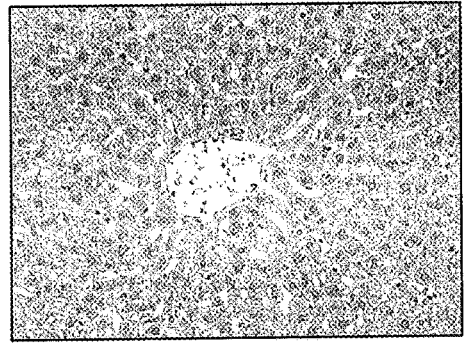
FIG. 4A is a light micrograph showing normal hepatocytes of rats.
Figure 4B:
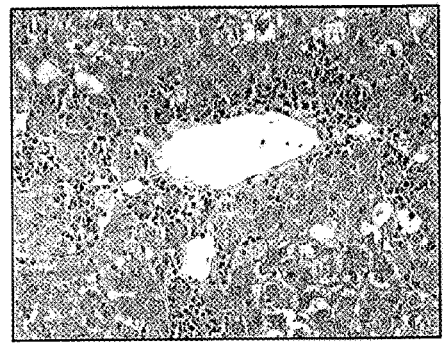
FIG. 4B is a light micrograph showing the effect of CCl$_4$-induced hepatotoxicity in hepatocytes of rats.
Figure 4C:
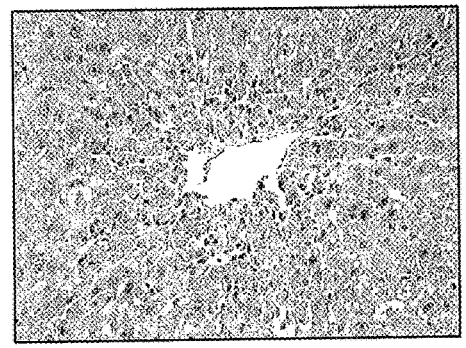
FIG. 4C is a light micrograph showing the effect of DHPB-2 on CCl$_4$-induced hepatotoxicity in hepatocytes of rats.
Figure 4D:
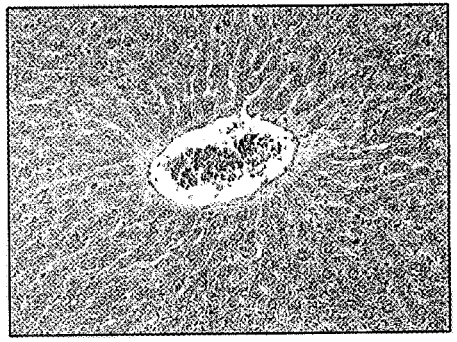
FIG. 4D is a light micrograph showing the effect of DHPB-2 on CCl$_4$-induced hepatotoxicity in hepatocytes of rats.
Figure 4E:
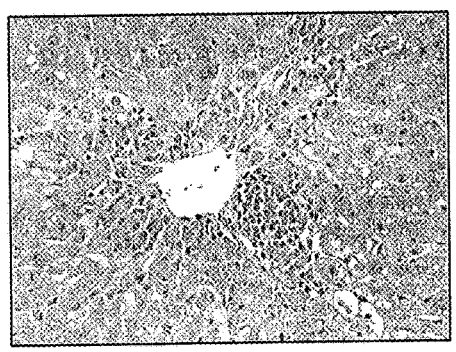
FIG. 4E is a light micrograph showing the effect of silymarin on CCl$_4$-induced hepatotoxicity in hepatocytes of rats.

Antihepatotoxic agents are useful agents for the treatment or prevention of liver diseases. The antihepatotoxic agents include dihydropyrimidinone derivatives with 1,4-benzodioxane. For example, the antihepatotoxic agents include 5-(2,3-dihydro-1,4-benzodioxine-6-carbonyl)-4-(substituted phenyl-3,4-dihydropyrimidin-2(1H)-one derivatives having the structure represented by Formula 1:

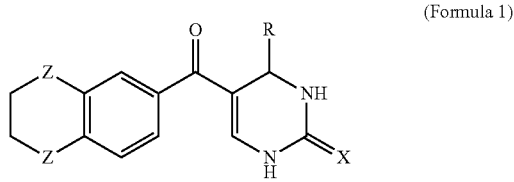

(Formula 1)

wherein Z represents O or N or S; X represents O or S; R represents aryl, substituted aryl, heteroaryl, or substituted heteroaryl; or a pharmaceutically acceptable salt thereof and associated pharmaceutical composition in therapy, in particular for the treatment or prevention of acute viral hepatitis, chronic viral hepatitis, liver cirrhosis and drug induced liver damage. Substituted aryl can be 2-nitro phenyl; 3-nitro phenyl; 4-nitro phenyl; 4-chloro phenyl; 3,4-dimethoxy phenyl; 2-methoxy phenyl; 3-methoxy phenyl; 4-methoxy phenyl; or 4-ethoxy phenyl. The substituted heteroaryl can be heteroaryl substituted with halogen, alyl, haloalyl, alkoxy, haloalkoxy, alkylthio, alkylamino, heteroaryl, aryloxy, haloaryloxy, arylthio, or arylamino.

The compounds of Formula 1 can be used as antihepatotoxic agents or as agents for treating or preventing acute or chronic viral hepatitis, liver cirrhosis, or drug-induced liver damage. The present subject matter also includes pharmaceutical formulations in dosage units.

The antihepatotoxic agents or pharmaceutical compositions including the antihepatotoxic agents can be administered to a subject by any suitable route. For example, the compositions can be administered orally (including bucally and sublingually), nasally, rectally, parenterally, intracisternally, intra vaginally, intraperitoneally, topically and transdermally (as by powders, ointments, or drops). The term "parenteral" administration as used herein refers to modes of administration other than through the gastrointestinal tract, which include intravenous, intramuscular, intraperitoneal, intrasternal, intramammary, intraocular, retrobulbar, intrapulmonary, intrathecal, subcutaneous and intraarticular injection and infusion. Surgical implantation also is contemplated, including, for example, embedding a composition of the disclosure in the body such as, for example, in a tissue, in the abdominal cavity, under the splenic capsule, brain, or in the cornea. Accordingly, the route of administration can include: intranasal administration; oral administration; inhalation administration; subcutaneous administration; transdermal administration; intradermal administration; intraarterial administration, with or without occlusion; intracranial administration; intraventricular administration; intravenous administration; buccal administration; intraperitoneal administration; intraocular administration; intramuscular administration; implantation administration; topical administration, intratumor administration and/or central venous administration.

Also provided is a pharmaceutical composition including one or more of the antihepatotoxic agents for treatment or prevention of liver diseases. To prepare the pharmaceutical composition, one or more of the antihepatotoxic agents or a salt thereof, as the active ingredient, is intimately admixed with a pharmaceutically acceptable carrier according to conventional pharmaceutical compounding techniques. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents and the like. For solid oral preparations, suitable carriers and additives include starches, sugars, diluents, granulating agents, lubricants, binders, disintegrating agents and the like. For parenteral use, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. Accordingly, the pharmaceutically acceptable carrier can include alcohol, dimethyl sulfoxide (DMSO), a physiological saline, a lipid based formulation, a liposomal formulation, a nanoparticle formulation, a micellar formulation, a water soluble formulation, a biodegradable polymer, an aqueous preparation, a hydrophobic preparation, a lipid based vehicle, or a polymer formulation.

The antihepatotoxic agents of the present disclosure also can be administered in the form of liposomes. As is known in the art, liposomes generally are derived from phospholipids or other lipid substances. Liposomes are formed by mono- or multi-lamellar hydrated liquid crystals that are dispersed in an aqueous medium. Any nontoxic, physiologically acceptable and metabolizable lipid capable of forming liposomes can be used. The present compositions in liposome form can include, in addition to a compound of the present disclosure, stabilizers, preservatives, excipients, and the like. The preferred lipids are the phospholipids and the phosphatidyl cholines (lecithins), both natural and synthetic.

Pharmaceutical compositions for parenteral injection can include pharmaceutically acceptable sterile aqueous or nonaqueous solutions, dispersions, suspensions, or emulsions, as well as sterile powders for reconstitution into sterile injectable solutions or dispersions just prior to use. Examples of suitable aqueous and nonaqueous carriers, diluents, solvents, or vehicles include water ethanol, polyols (such as, glycerol, propylene glycol, polyethylene glycol, and the like), and suitable mixtures thereof, vegetable oils (such, as olive oil), and injectable organic esters such as ethyl oleate. Proper fluidity can be maintained, for example, by the use of coating materials such as lecithin, by the maintenance of the required particle size in the case of dispersions, and by the use of surfactants.

The present compositions can include adjuvants such as preservatives, wetting agents, emulsifying agents, and dispersing agents. Prevention of the action of microorganisms can be ensured by the inclusion of various antibacterial and antifungal agents, for example, paraben, chlorobutanol, phenol sorbic acid, and the like. It also may be desirable to include isotonic agents such as sugars, sodium chloride, and the like. Prolonged absorption of the injectable pharmaceutical form can be brought about by the inclusion of agents which delay absorption, such as aluminum monostearate and gelatin. In some cases, in order to prolong the effect of the drug, it is desirable to slow the absorption of the drug from subcutaneous or intramuscular injection. This result can be accomplished by the use of a liquid suspension of crystalline or amorphous materials with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

The present compositions can be in unit dosage forms such as tablets, pills, capsules, powders, granules, ointments, sterile parenteral solutions or suspensions, metered aerosol or liquid sprays, drops, ampules, auto-injector devices or suppositories, for oral parenteral, intranasal, sublingual or rectal administration, or for administration by inhalation or insufflation. The active compound is mixed under sterile conditions with a pharmaceutically acceptable carrier and any needed preservatives, buffers, or propellants which may be required. The composition can be presented in a form suitable for daily, weekly or monthly administration. The pharmaceutical compositions herein will contain, per dosage unit, e.g., tablet, capsule, powder, injection, teaspoonful, suppository and the like, an amount of the active ingredient necessary to deliver an effective dose.

The following examples illustrate the present teachings.

Example 1

Synthesis of Compounds of Formula 1

Compounds of Formula 1 were synthesized according to the reaction scheme shown in FIG. 1. As shown in FIG. 1, the enaminone (III), (2E)-1-(2,3-dihydro-1,4-benzodioxin-6-yl)-3-(dimethylamino)-prop-2-en-1-one was synthesized by refluxing (I) 1-(2,3-dihydro-1,4-benzodioxin-6-yl)ethan-1-one with dimethylforamide dimethylacetal (DMF-DMA) (II) under solvent free condition for 10 hrs. The structure of the isolated product was confirmed by elemental analysis and spectral data. To prepare the final dihydropyrimidinone derivatives, a solution of enaminone (III) (0.01 mol), substituted benzaldehyde (0.01 mol), urea (0.01 mol) and Glacial acetic acid (10 mL) was heated under reflux for 3 hrs. The precipitates (compounds of Formula 1) formed were collected by filtration, washed with water, and recrystallized from Glacial acetic acid and ethanol mixture. In the 1H-NMR spectra, the signals of the individual protons of the compounds were verified on the basis of multiplicity, chemical shifts, and the coupling constant.

Example 2

Compounds of Formula 1

Exemplary compounds of Formula 1 were prepared and identified as DHPB-1 to DHPB-10 shown below:

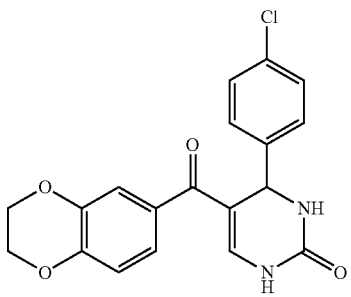

DHPB-1

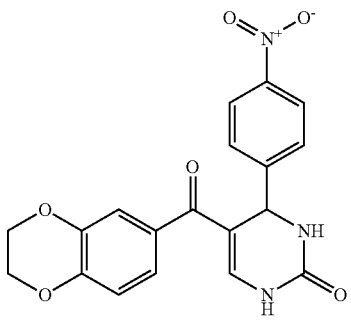

DHPB-2

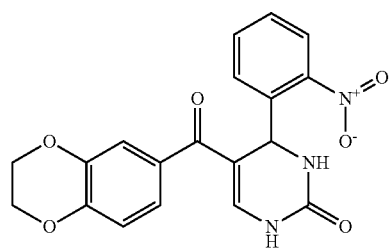

DHPB-3

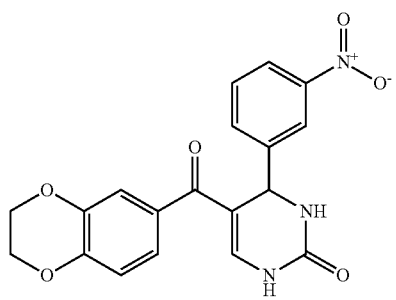

DHPB-4

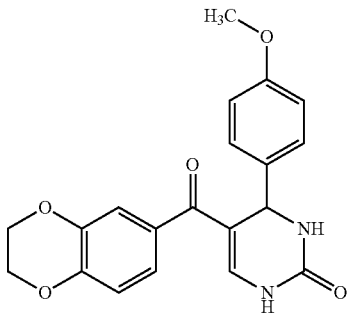

DHPB-5

-continued

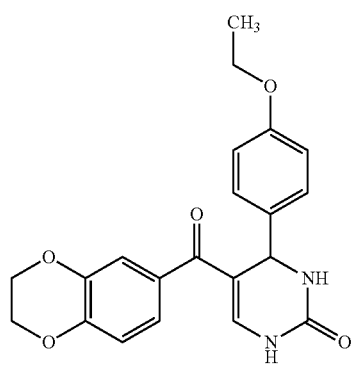
DHPB-6

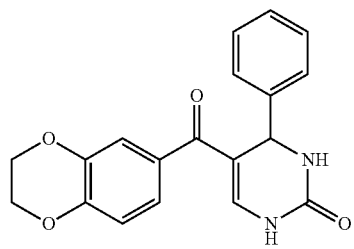
DHPB-7

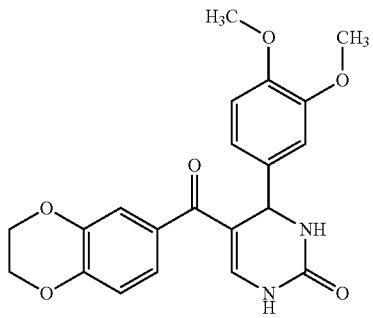
DHPB-8

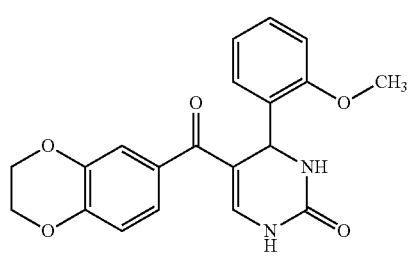
DHPB-9

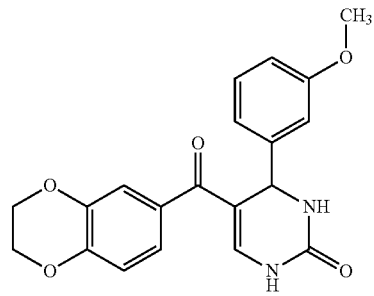
DHPB-10

The spectral data for the compounds DHPB-1 to DHPB-7, DHPB-9, and DHPB-10 are provided below.

4-(4-chlorophenyl)-5-(2,3-dihydro-1,4-benzodioxin-6-ylcarbonyl)-3,4-dihydropyrimidin-2(1H)-one DHPB-1: Yield: 80%; m.p.: 220-222° C.; IR (KBr) cm$^{-1}$: 3412 (NH str.), 1700 (C=O), 1654 (C=O), 1618 (C=C), 1196 (C—O); $^1$H NMR (500 MHz, DMSO-d$_6$): δ=4.27 (4H, s, 2×-OCH$_2$), 5.41 (1H, d, J=3.0 Hz, H-4), 6.90-7.30 (7H, m, Ar—H), 7.85 (1H, s, =CH), 9.33 (1H, bs, —NH, D$_2$O exchg.), 10.0 (1H, bs, —NH, D$_2$O exchg.); $^{13}$C NMR (125.76 MHz, DMSO-d$_6$): δ=53.5, 56.5, 64.4, 64.8, 65.3, 112.2, 117.3, 117.6, 122.3, 128.8, 128.9, 131.9, 132.3, 141.3, 143.5, 146.6, 151.6, 190.4; MS: m/z=370.77 [M]$^+$; Analysis: for C$_{19}$H$_{15}$ClN$_2$O$_4$, calcd. C, 61.55, H, 4.08, N, 7.56%; found C, 61.31, H, 4.09, N, 7.58%.

4-(4-Nitrophenyl)-5-(2,3-dihydro-1,4-benzodioxin-6-ylcarbonyl)-3,4-dihydro-pyrimidin2(1H)-one DHPB-2: Yield: 85%; m.p.: 198-200° C.; IR (KBr) cm$^{-1}$: 3244 (NH str.), 1699 (C=O), 1617 (C=O), 1588 (C=C), 11286 (C—O); $^1$H NMR (500 MHz, DMSO-d$_6$): δ=4.27 (4H, s, 2×-OCH$_2$), 5.54 (1H, d, J=3.0 Hz, H-4), 6.90-7.96 (7H, m, Ar—H), 8.21 (1H, s, =CH), 9.45 (1H, bs, —NH, D$_2$O exchg.), 10.2 (1H, bs, —NH, D$_2$O exchg.); $^{13}$C NMR (125.76 MHz, DMSO-d$_6$): δ=53.8, 56.5, 64.4, 64.8, 65.3, 111.6, 117.6, 117.3, 117.7, 122.3, 124.3, 128.3, 131.8, 141.8, 143.4, 146.7, 147.2, 151.4, 151.6; MS: m/z=381.34 [M]$^+$; Analysis: for C$_{19}$H$_{15}$N$_3$O$_6$, calcd. C, 59.84, H, 3.96, N, 11.02%; found C, 59.61, H, 3.95, N, 11.04%.

4-(2-Nitrophenyl)-5-(2,3-dihydro-1,4-benzodioxin-6-ylcarbonyl)-3,4-dihydro-pyrimidin-2(1H)-one DHPB-3: Yield: 85%; m.p.: 1180-182° C.; IR (KBr) cm$^{-1}$: 3411 (NH str.), 1700 (C=O), 1654 (C=O), 1611 (C=C), 1285 (C—O); $^1$H NMR (500 MHz, DMSO-d$_6$): δ=4.2 (4H, s, 2×-OCH$_2$), 5.5 (1H, d, J=2.5 Hz, H-4), 6.9-7.9 (7H, m, Ar—H), 8.1 (1H, s, =CH), 9.5 (1H, bs, —NH, D2O exchg.), 10.2 (1H, bs, —NH, D2O exchg.); $^{13}$C NMR (125.76 MHz, DMSO-d6): δ=53.6, 64.4, 64.8, 65.3, 111.5, 117.3, 117.7, 121.6, 122.3, 122.9, 130.7, 131.8, 133.7, 142.1, 143.4, 146.6, 146.7, 148.2, 151.4, 190.4; MS: m/z=381.35 [M]$^+$; Analysis: for C$_{19}$H$_{15}$N$_3$O$_6$, calcd. C, 59.84, H, 3.96, N, 11.02%; found C, 59.65, H, 3.97, N, 11.05%.

4-(3-Nitrophenyl)-5-(2,3-dihydro-1,4-benzodioxin-6-ylcarbonyl)-3,4-dihydro-pyrimidin-2(1H)-one DHPB-4: Yield: 80%; m.p.: 193-195° C.; IR (KBr) cm$^{-1}$: 3412 (NH str.), 1699 (C=O), 1617 (C=O), 1587 (C=C), 1286 (C—O); $^1$H NMR (500 MHz, DMSO-d$_6$): δ=4.2 (4H, s, 2×-OCH$_2$), 5.5 (1H, d, J=2.5 Hz, H-4), 6.9-7.9 (7H, m, Ar—H), 8.1 (1H, s, =CH), 9.5 (1H, bs, —NH, D$_2$O exchg.), 10.2 (1H, bs, —NH, D$_2$O exchg.); $^{13}$C NMR (125.76 MHz, DMSO-d$_6$): δ=53.6, 64.4, 64.8, 65.3, 111.5, 117.3, 117.7, 121.6, 122.3, 122.9, 130.7, 131.8, 133.7, 142.1, 143.4, 146.6, 146.7, 148.2, 151.4, 190.4; MS: m/z=381.30 [M]$^+$; Analysis: for C$_{19}$H$_{15}$N$_3$O$_6$, calcd. C, 59.84, H, 3.96, N, 11.02%; found C, 59.67, H, 3.94, N, 11.03%.

4-(4-Methoxyphenyl)-5-(2,3-dihydro-1,4-benzodioxin-6-ylcarbonyl)-3,4-dihydro-pyrimidin-2 (1H)-one DHPB-5: Yield: 65%; m.p.: 225-227° C.; IR (KBr) cm$^{-1}$: 3412 (NH str.), 1700 (C=O), 1654 (C=O), 1617 (C=C), 1287 (C—O); $^1$H NMR (500 MHz, DMSO-d$_6$): δ=3.7 (3H, s, —OCH$_3$), 4.2 (4H, s, 2×-OCH$_2$), 5.3 (1H, d, J=2.5 Hz, H-4), 6.8-7.2 (7H, m, Ar—H), 7.8 (1H, s, =CH), 9.2 (1H, bs, —NH, D$_2$O exchg.), 10.0 (1H, bs, —NH, D$_2$O exchg.); $^{13}$C NMR (125.76 MHz, DMSO-d$_6$): δ=53.4, 55.5, 60.2, 64.4, 64.8, 112.9, 114.2, 117.2, 117.6, 123.3, 128.0, 129.1, 132.1, 136.7, 140.7, 143.4, 146.5, 151.7, 159.0, 190.5, 206.9; MS: m/z=366.35 [M]$^+$; Analysis: for C$_{20}$H$_{18}$N$_2$O$_5$, calcd. C, 65.57, H, 4.95, N, 7.65%; found C, 65.79, 4.96, 7.68%.

4-(4-Ethoxyphenyl)-5-(2,3-dihydro-1,4-benzodioxin-6-ylcarbonyl)-3,4-dihydro-pyrimidin-2(1H)-one DHPB-6: Yield: 66%; m.p.: 210-212° C.; IR (KBr) cm$^{-1}$: 3420 (NH str.), 1700 (C=O), 1654 (C=O), 1617 (C=C), 1218 (C—O); $^1$H NMR (500 MHz, DMSO-d$_6$): δ=1.3 (3H, s, —CH$_3$), 4.0 (2H, s, —OCH$_2$), 4.2 (4H, s, 2×-OCH$_2$), 5.3 (1H, d, J=3.0 Hz, H-4), 6.7-7.3 (7H, m, Ar—H), 7.7 (1H, s, =CH), 9.2 (1H, bs, —NH, D$_2$O exchg.), 9.9 (1H, bs, —NH, D$_2$O exchg.); $^{13}$C NMR (125.76 MHz, DMSO-d$_6$): δ=19.0, 53.3, 56.5, 63.2, 63.4, 64.4, 64.8, 113.0, 114.3, 116.6, 117.2, 119.2, 122.3, 128.0, 129.0, 132.1, 136.6, 138.3, 139.6, 140.7, 143.3, 146.5, 151.7, 158.2, 190.5, 192.9; MS: m/z=380.40 [M]$^+$; Analysis: for C$_{21}$H$_{20}$N$_2$O$_5$, calcd. C, 66.31, H, 5.30, N, 7.36%; found C, 66.57, H, 5.31, N, 7.38%.

5-(2,3-dihydro-1,4-benzodioxin-6-ylcarbonyl)-4-phenyl-3,4-dihydropyrimidin-2(1H)-one DHPB-7: Yield:70%; m.p.: 250-252° C.; IR (KBr) cm$^{-1}$: 3412 (NH str.), 1706 (C=O), 1654 (C=O), 1617 (C=C), 1288 (C—O); $^1$H NMR (500 MHz, DMSO-d$_6$): δ=4.2 (4H, s, 2×-OCH$_2$), 5.4 (1H, d, J=2.0 Hz, H-4), 6.8-7.3 (8H, m, Ar—H), 7.8 (1H, s, =CH), 9.2 (1H, bs, —NH, D$_2$O exchg.), 10.0 (1H, bs, —NH, D$_2$O exchg.); $^{13}$C NMR (125.76 MHz, DMSO-d$_6$): δ=54.0, 56.5, 64.4, 64.8, 65.0, 112.7, 117.3, 117.6, 122.3, 126.8, 127.8, 128.9, 132.0, 141.0, 143.4, 144.5, 146.6, 151.7, 190.0; MS: m/z=396.42[M]$^+$; Analysis: for C$_{19}$H$_{16}$N$_2$O$_4$, calcd. C, 67.85, H, 4.79, N, 8.33%; found C, 67.59, H, 4.80, N, 8.36%.

4-(2-Methoxyphenyl)-5-(2,3-dihydro-1,4-benzodioxin-6-ylcarbonyl)-3,4-dihydro-pyrimidin-2(1H)-one DHPB-9: Yield: 50%; m.p.: 200-202° C.; IR (KBr) cm$^{-1}$: 3412 (NH str.), 1700 (C=O), 1654 (C=O), 1617 (C=C), 1286 (C—O); $^1$H NMR (500 MHz, DMSO-d$_6$): δ=3.7 (3H, s, —OCH$_3$), 4.3 (4H, s, 2×-OCH$_2$), 5.6 (1H, d, J=2.5 Hz, H-4), 6.8-7.3 (7H, m, Ar—H), 7.8 (1H, s, =CH), 9.2 (1H, bs, —NH, D$_2$O exchg.), 10.3 (1H, bs, —NH, D$_2$O exchg.); $^{13}$C NMR (125.76 MHz, DMSO-d$_6$): δ=49.7, 55.9, 56.3, 64.4, 64.7, 111.2, 113.1, 117.3, 120.7, 121.1, 122.3, 128.0, 129.3, 131.1, 132.1, 141.5, 143.4, 146.5, 152.3, 157.3, 190.4; MS: m/z=366.35 [M]$^+$; Analysis: for C$_{20}$H$_{18}$N$_2$O$_5$, calcd. C, 65.57, H, 4.95, N, 7.65%; found C, 65.70, H, 4.94, N, 7.67%.

4-(3-Methoxyphenyl)-5-(2,3-dihydro-1,4-benzodioxin-6-ylcarbonyl)-3,4-dihydropyrimidin-2(1H)-one DHPB-10: Yield: 55%; m.p.: 230-232° C.; IR (KBr) cm$^{-1}$: 3336 (NH str.), 1710 (C=O), 1654 (C=O), 1617 (C=C), 1287 (C—O); $^1$H NMR (500 MHz, DMSO-d$_6$): δ=3.7 (3H, s, —OCH$_3$), 4.3 (4H, s, 2×-OCH$_2$), 5.4 (1H, d, J=3.0 Hz, H-4), 6.8-7.5 (7H, m, Ar—H), 7.8 (1H, s, =CH), 9.2 (1H, bs, —NH, D$_2$O exchg.), 9.9 (1H, bs, —NH, D$_2$O exchg.); $^{13}$C NMR (125.76 MHz, DMSO-d$_6$): δ=53.8, 55.4, 56.5, 64.4, 112.5, 113.4, 116.2, 117.2, 118.9, 119.3, 121.4, 122.3, 129.8, 130.8, 132.0, 138.1, 141.1, 143.4, 146.0, 151.8, 159.7, 160.2, 172.4, 190.5; MS: m/z=366.31 [M]$^+$; Analysis: for C$_{20}$H$_{18}$N$_2$O$_5$, calcd. C, 65.57, H, 4.95, N, 7.65%; found C, 65.72, H, 4.96, N, 7.63%.

Example 3

Toxicity and Efficacy of Formula 1 Compounds

Acute toxicity test: The acute toxicity test was performed on mice, for oral administration. DHPB-2 was dissolved in 0.5% CMC (carboxymethylcellulose) in water and administered at various doses, ranging from (10-200 mg/kg), to different groups of mice. The animals were observed continuously for 1 h and then at half hourly intervals for 4 h on the first day for clinical signs and symptoms of toxicity, and further up to 72 h followed by 14 days, for any mortality.

Animals and study design: Wistar albino rats (180-200 g) were obtained from the Experimental Animal Care Center of the College of Pharmacy, King Saud University, Riyadh. Animals were maintained on standard chow diet and housed in polycarbonate cages in a room free from any source of chemical contamination, artificially illuminated (12 h dark/light cycle) and thermally controlled (25±2° C.) at the animal facility. All animals received humane care in compliance with the guidelines of the Ethics Committee of the Experimental Animal Care Society, College of Pharmacy, King Saud University, Riyadh, Saudi Arabia. After a one-week acclimatization period, animals were randomly allocated into 5 groups and treated as follows: group (1), untreated control; and groups 2, 3, 4, and 5 received 0.25 mL of CCl$_4$ in liquid paraffin (1:1) 1.25 mL/kg body weight intraperitoneally (IP). Group 2 was administered only CCl$_4$. Groups 3 and 4 received DHBP-2 (10 mg/kg) and (20 mg/kg/day) orally for 2 weeks, respectively. Rats in group 5 were treated with (10 mg/kg) orally with silymarin for similar days. The blood was collected by cardiac puncture after 24 hours following the administration of CCl$_4$, allowed to clot, and the serum was then separated. After collecting the blood, the animals were sacrificed using ether anesthesia. The rat livers were dissected out and used for biochemical estimations and histological assessment.

Estimation of marker enzymes: Serum glutamate oxaloacetate transaminase (SGOT/AST), serum glutamate pyruvate transaminase (SGPT/ALT) (Reitman S. A. et al., Am. J. Clin. Pathol. 1957, 28 (1), 56-63), alkaline phosphatase (ALP), gamma-glutamyl transferase (GGT) and bilirubin were determined using Reflotron Plus Analyzer and Roche kits (Roche Diagnostics GmbH, Mannheim, Germany) (King E. J. et al., Practical Clinical Biochemistry, H. Varley, Ed., CBS publishers, New Delhi, India, 1988).

Determination of malondialdehyde (MDA): The method reported by (Utley H. C. et al., Archives of Biochemistry Biophysics, 1967, 260, 521-531) was followed. Briefly, the liver tissues were removed, and tissue was homogenized in 0.15 M KCl (at 4° C.; Potter-Elvehjem type C homogenizer) to give a 10% w/v homogenate. The absorbance of the solution was then read at 532 nm. The content of malondialdehyde (nmol/g wet tissue) was then calculated, by reference to a standard curve of malondialdehyde solution.

Estimation of non-protein sulfhydryls (NP-SH): Hepatic non-protein sulfhydryls were measured according to the method of Sedlak and Lindsay et. al., Analytical Biochemistry C, 1968, 25, 192-205. The livers were homogenized in ice-cold 0.02 mmol/L ethylenediaminetetraacetic acid (EDTA). The absorbance was measured within 5 min. of addition of 5,5'-dithio-bis(2-nitrobenzoic acid) (DTNB) at 412 nm against a reagent blank.

Determination of total protein (TP): Total protein was estimated by the kit method, supplied by Crescent Diagnostics, Jeddah, Saudi Arabia. The absorbance of this complex at 546 nm is proportional to the protein concentration. The serum total protein was calculated using the equation:

Serum total protein=ABS sample/ABS standard× concentration of standard.

Histopathological evaluation: The liver tissue samples were fixed in neutral buffered formalin for 24 h. Sections of the liver tissue were histopathologically examined. These sections were stained with hematoxylin and eosin using routine procedures (Culling C. F. Handbook of Histopathological and Histochemical Techniques, Butterworth, London, UK, 3rd edition, 1974).

Statistical analysis: Values in tables and figures are given as mean±SE. Data were analyzed by using one-way analysis of variance (ANOVA) followed by Student's t-test.

Acute toxicity test results: No toxicity symptoms and no morbidity were observed up to 500 mg/kg of the compound DHPB-2 in the animals.

In vivo effect of DHPB-2 on liver: The results indicated that animals treated with $CCl_4$ showed a significant increase in all biochemical parameters tested. However, animals treated with DHPB-2 (20 mg/kg) for 2 weeks before intoxication with $CCl_4$ showed a significant decrease in AST, ALT, ALP, GGT and bilirubin levels as shown in FIGS. 2A-2B. $CCl_4$-induced oxidative stress caused an elevation in lipid profile including cholesterol, triglycerides, LDL cholesterol and VLDL cholesterol and reduction in the HDL cholesterol levels in serum. The two week pretreatment of rats with DHPB-2 (20 mg/kg) significantly reduced the cholesterol, triglycerides, LDL cholesterol, and VLDL cholesterol levels and significantly improved HDL cholesterol level as shown in FIGS. 3A-3B. Silymarin, on the other hand, significantly prevented the $CCl_4$-induced elevated levels of marker enzymes and lipid profile. The results also indicated that treatment with $CCl_4$ resulted in a significant increase in MDA and a significant decrease in NP-SH and TP concentration in liver tissues as provided in Table 1 below.

TABLE 1

Effect of DHPB-2 on MDA, NP-SH and total protein in liver tissue

| Treatments (n = 6) | Dose (mg/kg) | MDA (nmol/g) | NP-SH (nmol/g) | Total Protein (g/L) |
|---|---|---|---|---|
| Normal | — | 0.46 ± 0.01 | 7.28 ± 0.28 | 126.43 ± 7.81 |
| $CCl_4$ | 1.5 mL | 8.56 ± 0.43*** [a] | 3.78 ± 0.19*** [a] | 30.85 ± 1.28*** [a] |
| Silymarin + $CCl_4$ | 10 | 1.09 ± 0.05*** [b] | 7.36 ± 0.67*** [b] | 88.45 ± 5.53*** [b] |
| DHPB-2 + $CCl_4$ | 10 | 6.84 ± 0.52* [b] | 4.30 ± 0.33 [b] | 38.11 ± 3.09 [b] |
| DHPB-2 + $CCl_4$ | 20 | 1.59 ± 0.13*** [b] | 6.16 ± 0.31*** [b] | 74.03 ± 4.36*** [b] |

All values represent mean ± SEM. *p < 0.05; ***p < 0.001; ANOVA, followed by Dunnett's multiple comparison test.
[a] As compared with Normal group.
[b] As compared with $CCl_4$ group.

Treatment of rats with DHPB-2 (20 mg/kg) resulted in significant reduction in the level of MDA and significantly enhanced the NP-SH and TP levels in liver tissue. Upon histopathological assessment of the liver, the $CCl_4$-induced rats showed evidence of fatty changes with necrosis in liver cells, extensive fatty and inflammatory changes along with vascular congestion, and minimal fibrosis.

FIGS. 4A-4E illustrate light micrographs of hepatocytes in rats. The rats which received DHPB-2 (10 and 20 mg/kg/day) (FIGS. 4C and 4D) and silymarin (FIG. 4E), as oral pretreatment, showed a marked improvement in liver parenchyma with small degenerative changes of the cytoplasm and completely intact liver hepatocytes.

Biological evaluation of the synthesized Formula 1 compounds of the present subject matter revealed that the compounds possess remarkable antihepatotoxic activity. The obtained results clearly point to the discovery of a new group of antihepatotoxic agents. The compounds of Formula 1 have potential use as antihepatotoxic agents, comparable to the standard antihepatotoxic drug, silymarin.

It is to be understood that the present subject matter is not limited to the embodiments described above, but encompasses any and all embodiments within the scope of the following claims.

We claim:

1. A compound having the structure of Formula 1:

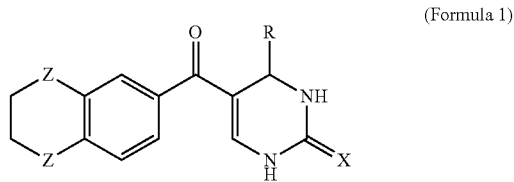

(Formula 1)

wherein:
each Z independently represents O or S;
X represents O or S; and
R represents aryl, substituted aryl, heteroaryl, or substituted heteroaryl;
or a pharmaceutically acceptable salt thereof.

2. The compound of claim 1, wherein R is 2-nitro phenyl, 3-nitro phenyl, 4-nitro phenyl, 4-chloro phenyl, 3,4-dimethoxy phenyl; 2-methoxy phenyl, 3-methoxy phenyl, 4-methoxy phenyl, or 4-ethoxy phenyl.

3. The compound of claim 1, wherein R is a heteroaryl substituted with halogen, alyl, haloalyl, alkoxy, haloalkoxy, alkylthio, alkylamino, heteroaryl, aryloxy, haloaryloxy, arylthio, or arylamino.

4. The compound of claim 1, wherein the compound is:

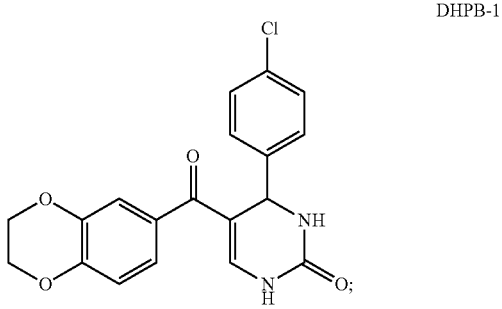

DHPB-1

DHPB-2
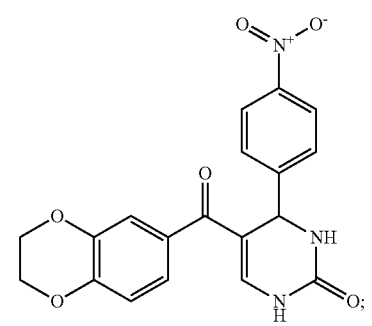

DHPB-3
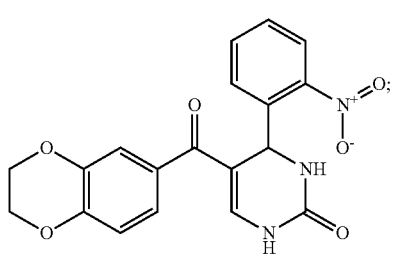

DHPB-4
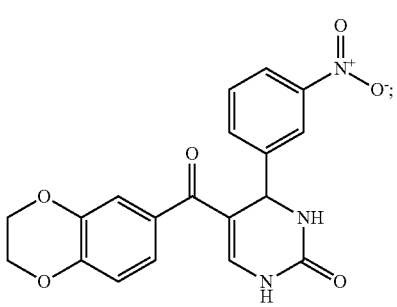

DHPB-5
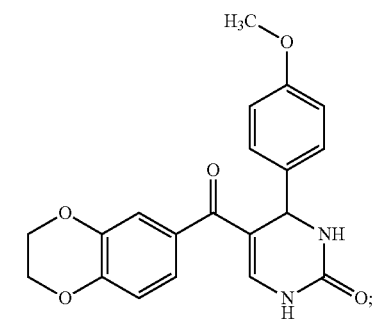

DHPB-6
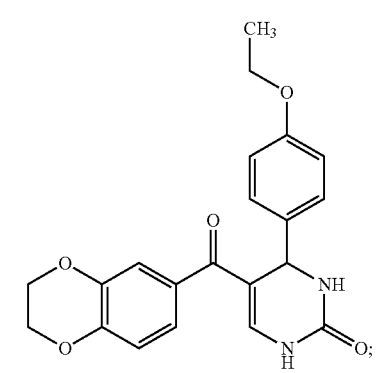

DHPB-7
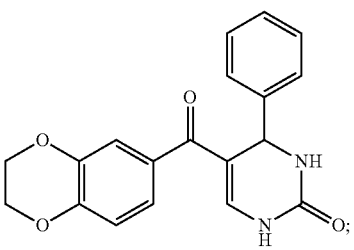

DHPB-8
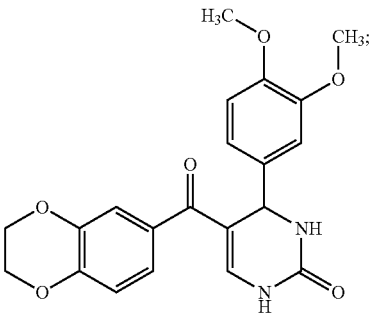

DHPB-9
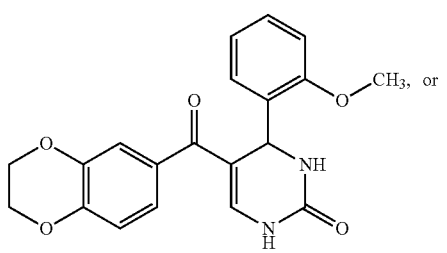

DHPB-10

5. A method of treating $CCl_4$-induced hepatotoxicity in a patient, comprising administering a compound of claim 1 to a patient in need thereof.

6. A method of treating $CCl_4$-induced hepatotoxicity in a patient, comprising administering a compound of claim 2 to a patient in need thereof.

7. A method of treating $CCl_4$-induced hepatotoxicity in a patient, comprising administering a compound of claim 3 to a patient in need thereof.

8. A pharmaceutical composition comprising at least one compound according to claim 1, and at least one non-toxic, inert, pharmaceutically suitable excipient.

9. A pharmaceutical composition comprising at least one compound according to claim 4, and at least one non-toxic, inert, pharmaceutically suitable excipient.

10. The pharmaceutical composition of claim 9, wherein the compound is 4-(4-nitrophenyl)-5-(2,3-dihydro-1,4-benzodioxin-6-ylcarbonyl)-3,4-dihydro-pyrimidin2(1H)-one.

11. A method of treating $CCl_4$-induced hepatotoxicity, comprising the step of administering to a patient the pharmaceutical composition of claim 8.

12. A method of treating CCl$_4$-induced, comprising the step of administering to a patient the pharmaceutical composition of claim 9.

13. A method of treating CCl$_4$-induced, comprising the step of administering to a patient the pharmaceutical composition of claim 10.

14. A method of preparing the compound of claim 1, comprising the steps of:
 (a) refluxing 1-(2,3-dihydro-1,4-benzodioxin-6-yl)ethan-1-one with dimethylform-amide dimethylacetal (DMF-DMA) to obtain enaminone;
 (b) preparing a solution of the enaminone, substituted benzaldehyde, and urea; and
 (c) refluxing the enaminone solution of step (b) to yield a compound of Formula 1, having the structure:

(Formula 1)

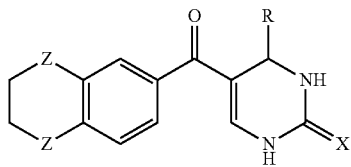

wherein:
 each Z independently represents O or S;
 X represents O or S;
 R represents aryl, substituted aryl, heteroaryl, or substituted heteroaryl;
 or a pharmaceutically acceptable salt thereof.

15. The method of claim 14, wherein R is 2-nitro phenyl, 3-nitro phenyl, 4-nitro phenyl, 4-chloro phenyl, 3,4-dimethoxy phenyl, 2-methoxy phenyl, 3-methoxy phenyl, 4-methoxy phenyl, or 4-ethoxy phenyl.

16. The method of claim 14, wherein R is heteroaryl substituted with halogen, alyl, haloalyl, alkoxy, haloalkoxy, alkylthio, alkylamino, heteroaryl, aryloxy, haloaryloxy, arylthio, or arylamino.

17. The method of claim 14, wherein the refluxing in step (a) is done under solvent free conditions for a period of about 10 hours.

18. The method of claim 14, wherein the refluxing in step (b) is done in the presence of glacial acetic acid, for a period of 3 hours.

19. The method of claim 14, further comprising recrystallizing the compound of Formula 1 from a mixture of ethanol and glacial acetic acid.

* * * * *